United States Patent
Young

(10) Patent No.: US 10,456,148 B2
(45) Date of Patent: Oct. 29, 2019

(54) BONE BROACH AND METHOD OF MANUFACTURING A BONE BROACH

(71) Applicant: DEPUY INTERNATIONAL LIMITED, Leeds, West Yorkshire (GB)

(72) Inventor: Duncan Young, Hebden Bridge (GB)

(73) Assignee: DEPUY INTERNATIONAL LIMITED (GB)

(*) Notice: Subject to any disclaimer, the term of this patent is extended or adjusted under 35 U.S.C. 154(b) by 226 days.

(21) Appl. No.: 15/497,277

(22) Filed: Apr. 26, 2017

(65) Prior Publication Data

US 2017/0224361 A1 Aug. 10, 2017

Related U.S. Application Data

(60) Continuation of application No. PCT/GB2012/052947, filed on Nov. 29, 2012, and a division of application No. 14/294,373, filed on Jun. 3, 2014, now Pat. No. 9,662,122, which is a (Continued)

(30) Foreign Application Priority Data

Dec. 1, 2011 (GB) .................................. 1120642.2

(51) Int. Cl.
*A61B 17/16* (2006.01)
*B23K 11/11* (2006.01)
*A61B 17/00* (2006.01)
*B23K 101/20* (2006.01)

(52) U.S. Cl.
CPC ...... *A61B 17/1659* (2013.01); *A61B 17/1668* (2013.01); *B23K 11/115* (2013.01); *A61B 2017/00526* (2013.01); *B23K 2101/20* (2018.08); *Y10T 29/49826* (2015.01); *Y10T 29/49895* (2015.01)

(58) Field of Classification Search
CPC ............ A61B 17/1662; A61B 17/1668; A61B 17/1659; A61B 17/1664
See application file for complete search history.

(56) References Cited

U.S. PATENT DOCUMENTS

| 143,413 A | 10/1873 | Jelliffe |
|---|---|---|
| 482,704 A | 9/1892 | Wall |
| 1,004,193 A | 9/1911 | Plaisted |

(Continued)

FOREIGN PATENT DOCUMENTS

| BE | 1015812 A3 | 9/2005 |
|---|---|---|
| DE | 102008020192 A1 | 10/2009 |

(Continued)

Primary Examiner — David W Bates

(57) ABSTRACT

A bone broach is formed from a plurality of substantially planar members which are positioned adjacent to each other with each of the substantially planar members attached to at least one other substantially planar member. At least some of the substantially planar members defines at least one cutting profile at its perimeter. The plurality of substantially planar members include a first group of substantially planar members defining planes which are substantially parallel to each other, and at least one additional substantially planar member defining a plane which is angled relative to the planes defined by the first group of substantially planar members.

12 Claims, 9 Drawing Sheets

Related U.S. Application Data continuation of application No. PCT/GB2012/052947, filed on Nov. 29, 2012.

(56) References Cited

U.S. PATENT DOCUMENTS

| | | | |
|---|---|---|---|
| 4,350,151 A | 9/1982 | Scott | |
| 4,466,429 A | 8/1984 | Loscher | |
| 4,739,750 A | 4/1988 | Masse | |
| 5,006,121 A | 4/1991 | Hafeli | |
| 5,124,106 A | 6/1992 | Morr | |
| 5,169,402 A | 12/1992 | Elloy | |
| 5,454,815 A | 10/1995 | Geisser | |
| 5,653,712 A | 8/1997 | Stern | |
| 6,120,508 A | 9/2000 | Grunig | |
| 6,168,599 B1 * | 1/2001 | Frieze | A61B 17/16 408/227 |
| 8,679,127 B2 | 3/2014 | Biegun | |
| 8,845,733 B2 | 9/2014 | O'Neil | |
| 9,011,446 B1 | 4/2015 | Henderson | |
| 9,247,944 B2 | 2/2016 | Fenn | |
| 2004/0116933 A1 | 6/2004 | White | |
| 2004/0249384 A1 | 12/2004 | Blaha | |
| 2004/0267266 A1 | 12/2004 | Daniels | |
| 2007/0276393 A1 | 11/2007 | Bonadei | |
| 2010/0168752 A1 | 7/2010 | Edwards | |
| 2015/0005777 A1 | 1/2015 | Ferro | |
| 2016/0166261 A1 | 6/2016 | Kleiner | |
| 2016/0175109 A1 | 6/2016 | Reu | |
| 2016/0235417 A1 | 8/2016 | Duncan | |

FOREIGN PATENT DOCUMENTS

| | | |
|---|---|---|
| DE | 102008020199 A1 | 10/2009 |
| EP | 1987785 A2 | 11/2008 |
| FR | 2547192 A1 | 12/1984 |
| JP | 2007534356 A | 11/2007 |
| JP | 2011521718 A | 7/2011 |

* cited by examiner

BONE BROACH AND METHOD OF MANUFACTURING A BONE BROACH

This application is a divisional of U.S. patent application Ser. No. 14/294373 filed Jun. 3, 2014 which is a continuation of International Patent Application PCT/GB2012/052947 filed Nov. 29, 2012, which claims priority to United Kingdom Application No. GB1120642.2, filed Dec. 1, 2011 (now abandoned), all of which are incorporated by reference in their entireties.

The present invention relates to a bone broach for broaching the inside of a bone in preparation to receive an implant. The invention also relates to a method of manufacturing a bone broach.

Bone broaches are used in surgery to broach a cavity within a bone, for example a femur, to create a cavity with dimensions for receiving an implant. It is known to produce bone broaches by machining a single piece of metal or metal alloy. The cost of production is relatively high, but a bone broach can be produced reliably with the desired profile that closely matches the implant. Bone broaches produced in this way are known and trusted by surgeons. Their high cost means they are reused and must be decontaminated/sterilised after use.

Depending on the final size of the opening required for an implant, a number of broaches of successively increasing sizes may be required. Each broach enlarges the opening slightly until the final broach matches the size of the implant. For example, when broaching a femur for a small implant, two broaches may be required. For a medium sized femoral implant, four broaches may be needed. A large size femoral implant may require seven broaches.

It would be desirable to reduce the cost of bone broaches, so that it is economical to provide single use instruments, avoiding the cost of decontamination and sterilisation after use.

U.S. Pat. No. 5,006,121 describes a bone broach which comprises a longitudinal support mandrel. The profile of the broach is defined by a plurality of broach plates stacked onto the mandrel so that the stack of plates define the shape of the broach. The plates are stacked so that they define the planes which are perpendicular to the longitudinal axis of the mandrel. In use, the broach is reciprocated along the longitudinal axis.

The construction disclosed in U.S. Pat. No. 5,006,121 allows broaches to be produced with tailored profiles. However, the arrangement of the broach plates perpendicular to the axis of the instrument gives rise to a risk that plates can become disconnected from each other or the mandrel in use. In use the force along the axis acts perpendicular to the plates, providing sometimes significant forces which may cause them to disconnect from adjacent plates. This disadvantage is acknowledged in the document, which mentions that it is desirable to be able to retrieve broach plates from within the bone in the event that the bond between them fails.

It would be desirable to provide a bone broach which is relatively inexpensive to manufacture, so that single use bone broaches can be provided for surgery.

The present invention provides a bone broach comprising a plurality of substantially planar members which are divided into at least first and second groups. The planes defined by the substantially planar members within each group are parallel to each other and the plane or planes defined by the second group at an angle relative to the first group. This reduces the risk of disconnection between the plates during use, compared to the construction disclosed in U.S. Pat. No. 5,006,121.

Accordingly, the invention provides a bone broach comprising a plurality of substantially planar members which are positioned adjacent to each other. Each of the substantially planar members is attached to at least one other substantially planar member, and at least some of the substantially planar members defines at least one cutting profile at its perimeter. The plurality of substantially planar members comprises: a first group of substantially planar members defining planes which are substantially parallel to each other; and at least one additional substantially planar member defining a plane which is angled relative to the planes defined by the first group of substantially planar members. The cutting profile may include one or more cutting edges and/or other configurations across the depth of the substantially planar member. The cutting profile may be for use in a direction along a longitudinal axis. In some constructions, the bone broach may further comprise planar members which do not define a cutting profile.

t will frequently be preferred for the additional substantially planar member to be one of a second group of planar members, the second group of planar members which define planes which are substantially parallel to one another in the assembled broach, the planes defined by the second group of planar members being angled relative to the planes defined by the first group.

It will frequently be preferred for each of the plates of the first group to define one or more cutting profiles at its perimeter. It will frequently be preferred for the additional substantially planar member or each of some or all of the plates of the second group to define one or more cutting profiles at its perimeter.

Such construction provides a strong, easy to manufacture and inexpensive bone broach in which the risk of planar members remaining in the bone during use is minimised. A further benefit is that the range of possible tooth profiles is increased over the stacked plate constructions disclosed in U.S. Pat. No. 5,006,121 and also over prior art machined bone broaches.

The grouping of the substantially planar members allows them to be formed into stacks which define a volume and shape of an instrument generally corresponding to the volume and shape of an opening required to be formed in a bone by the bone broach.

In some embodiments, the planes defined by the substantially planar members of the first group, or of the second group, or of both the first group and the second group, may also be parallel to a longitudinal axis of the instrument. This will depend on the desired profile to be created by the instrument. Where the desired profile has an identifiable longitudinal axis, arranging the planes of the substantially planar members of bone or both groups parallel to the axis is particularly advantageous. However, other embodiments may not have a profile with an identifiable longitudinal axis, such as instruments intended to be moved along an arced path in use. In that case, it may not be advantageous or possible to arrange the planes of the substantially planar members parallel to a longitudinal axis.

Preferably, the plane defined by the additional substantially planar member is substantially perpendicular to the planes defined by the first group of substantially planar members. This can produce a stronger construction.

Similarly, it can be preferred that the planes defined second group of substantially planar members define planes which are substantially perpendicular to the planes defined by the first group of substantially planar members. This can produce a stronger construction.

In one embodiment, the first group may be aligned to provide medial and lateral cutting edges, with the second group providing cutting edges perpendicular to the medial and lateral edges.

Preferably, the first group and the additional substantially planar member or second group form interlocking stacks. The interlocking stacks may interlock the substantially planar members of the first group with the additional substantially planar member or substantially planar members of the second group. This improves the strength of the construction. It can also allow the bone broach to be constructed with the minimum of additional adhesive or joining required, further reducing construction cost.

Preferably, each substantially planar member of the first group defines at least one opening; and additional substantially planar member or each substantially planar member of the second group defines at least one protrusion for engaging an opening in at least one substantially planar member of the first group. The at least one opening preferably extends through the substantially planar member in a direction perpendicular to the plane it defines. This allows interlocking stacks to be achieved with a simple construction.

In one embodiment, at least one opening in each substantially planar member of the first group is aligned with an opening in a directly adjacent substantially planar member of the first group, thereby creating an aligned opening; and the additional substantially planar member or at least one substantially planar member of the second group comprises a protrusion with dimensions to engage the aligned opening. By creating aligned openings, a single protrusion can interlock with more than one plate, creating a stronger overall form and locking adjacent plates in the first group together.

Preferably, the aligned opening extends through the first group of substantially planar members in a direction perpendicular to the planes defined by the first group of substantially planar members. This simplifies ease of assembly, since it allows a generally straight protrusion to engage the aligned opening.

Optionally, the additional substantially planar member or at least one substantially planar member of the second group may comprise a protrusion having dimensions to extend through and out of the aligned opening. At least part of the protrusion which extends out of the opening defines at least one cutting profile. Thus, the protrusions can define cutting edges and fulfil a further purpose as well as interlocking the plates of the first group. This also allows cutting edges to be provided on opposite edges of the additional substantially planar member or of the second group of substantially planar members, on opposite sides of the first group.

Preferably, the plurality of substantially planar members in the first group, and in the second group when present, each directly abut another of the plurality of substantially planar members. This produces a solid construction with minimal gaps between individual members.

In an advantageous embodiment, the plurality of substantially planar members comprise a metal or metal alloy. The individual members may then be joined by spot welding at either side of a stack of the substantially planar members. This allows the bone broach to be manufactured in a cost-effective manner.

In one embodiment, at least one of the plurality of substantially planar members defines an opening such that the plurality of substantially planar members define a solid which is at least partially hollow. This provides that advantage that the bone broach is lighter than prior art broaches, making it easier to handle and reducing production and transport costs.

In further embodiments, the substantially planar members may divided into more than two groups, with the groups each defining parallel planes that are angled with respect to the planes defined by other groups. One or more of the groups other than the first group can each comprise one plate or a plurality of plates.

In another aspect, the invention provides a system of at least two bone broaches of different sizes. At least one bone broach is constructed as defined above, with or without the optional features also described. The system also comprises at least one additional bone broach which does not comprise a plurality of substantially planar members. For example, the at least one bone broach may be manufacturing by machining a single block of material. The bone broach constructed as discussed above is generally cheaper to manufacture and may be disposable, while a machined bone broach may be reusable. This combines the benefit of single use bone broaches with a reusable bone broach. It is particularly advantageous when the bone broach which does not comprise a plurality of substantially planar members is the largest size in the system, allowing it to be used for final finishing.

In another aspect, the invention provides a method of manufacturing a bone broach, the method comprising:

(a) preparing a plurality of substantially planar members of which at least some define at least one cutting profile at their perimeters, (b) arranging the plurality of substantially planar members into:

a first group of substantially planar members defining planes which are substantially parallel to each other, and at least one additional substantially planar member defining a plane which is angled relative to the planes defined by the first group of substantially planar members, and (c) joining the plurality of substantially planar members together.

This allows a cost-effective method of manufacturing a bone broach, which reduces cost of production so that a single use instrument is feasible.

The preparing may comprise cutting or etching from a sheet of material. It is currently preferred that chemical etching is used, although other cutting techniques may also be used, including laser cutting, stamping, water jet cutting, wiring, CNC machining, CNC punching and direct metal laser sintering. In general cutting techniques with lower cost are more preferable.

Preferably, the preparing comprises cutting or etching the plurality of substantially planar members from the same sheet of material. This allows improved quality control, since the same sheet of material is used to form all the elements of the bone broach. It also ensures uniformity in the thickness of each substantially planar member.

It will frequently be preferred for the additional substantially planar member to be one of a second group of planar members, the second group of planar members which define planes which are substantially parallel to one another in the assembled broach, the planes defined by the second group of planar members being angled relative to the planes defined by the first group.

In the arranging step, the additional substantially planar member or the second group of substantially planar members may define planes which are substantially perpendicular to the planes defined by the first group of substantially planar members. This allows a stronger structure to be achieved.

In some embodiments the first group of planar members and the additional substantially planar member or the second group of planar members may form interlocking stacks.

The preparing step may further comprise defining at least one opening in each substantially planar member of the first group; and defining at least one protrusion in the additional substantially planar member or in each substantially planar member of the second group; and the arranging then further comprises engaging an opening in at least one substantially planar member of the first group with the protrusion. This allows an interlocking stack to be provided, with the openings engaged with protrusions to interlock the groups together.

The arranging step may further comprise aligning at least one opening in each substantially planar member of the first group with an opening in a directly adjacent substantially planar member of the first group, thereby creating an aligned opening; and engaging the aligned opening with a protrusion of the additional substantially planar member or at least one substantially planar member of the second group. This enables the protrusion to interlock several members of the first group together and prevent movement within the plane they define.

Preferably, the arranging step includes aligning directly adjacent substantially planar members of the first group such that the aligned opening extends through the first group in a direction perpendicular to the planes defined by the first group. This enables easier construction because the protrusion can be inserted through a linear opening in the first group.

In some embodiments, the arranging further comprises engaging a protrusion of at least one substantially planar member of the second group with the aligned opening, such that the protrusion extends out of the opening and defines a cutting edge. This enables the members of the second group to define cutting edges on each side of the planar members of the first group.

Preferably, the plurality of substantially planar members each directly abut another of the plurality of substantially planar members, thereby forming a solid three-dimensional structure.

The plurality of substantially planar members preferably comprise a metal or metal alloy and the joining comprises spot welding. This enables the structure to be joined together in a cost-effective manner without requiring any additional adhesives or weld flux. This can improve the biocompatibility of the broach, because the only materials used will be the materials of the substantially planar members themselves.

In another aspect of the invention, there is provided a method of manufacturing a system of at least two bone broaches of different sizes, the method comprising manufacturing each bone broach according to the method discussed above (with or without the optional features also described), wherein the shape of at least one of the substantially planar members is the same in at least two of the bone broaches. This allows reuse of designs and simplifies construction.

Embodiments of the invention will now be described by way of example only with reference to the accompanying drawings in which.

Figure 1:
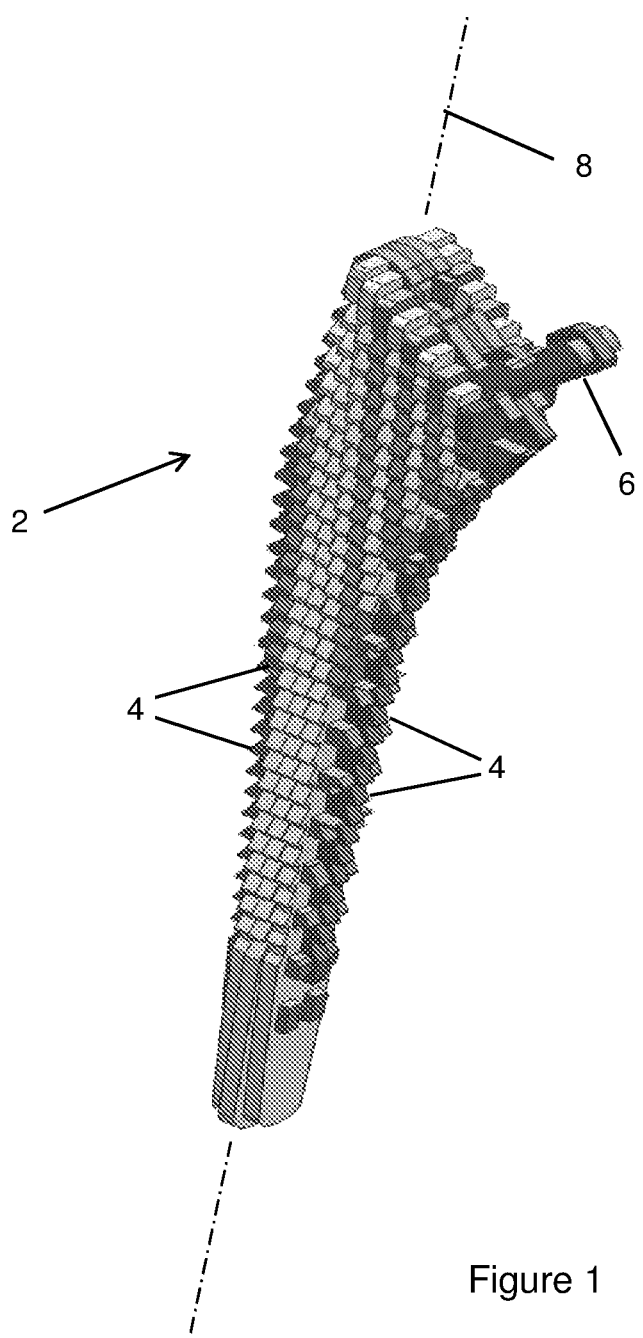
FIG. 1 is a perspective view of a bone broach according to an embodiment of the present invention.

Referring to the drawings, FIG. 1 is a perspective view of a bone broach 2 according to a first embodiment of the present invention. As will be explained in more detail subsequently, the bone broach comprises a plurality of substantially planar members or sheet members arranged adjacent each other to define a three-dimensional structure with an external profile corresponding to the shape required to be created in a bone by the broach. As shown in FIG. 1, the bone broach 2 is for broaching the inside of a femur in preparation for receiving an implant. Other embodiments may have other configurations depending on the bone to be broached and the configuration of the cavity that the broach is required to create.

The bone broach 2 comprises a plurality of cutting surfaces 4 which are defined by the edges of the sheet members making up the broach. The broach also comprises a stem 6 that can be used to grasp the broach and control it in use.

The bone broach 2 defines a longitudinal axis 8 along which the broach is inserted into and withdrawn from the bone to create the cavity. (Other embodiments, not shown, may be for use along a curved or arcing path, and in that case will not define a longitudinal axis.) All of the plurality of sheet members comprising the bone broach 2 are arranged so that they define a plane which is parallel to the longitudinal axis 8.

In this embodiment, the structure is strengthened by dividing the plurality of sheet members into two groups which define planes that are mutually perpendicular. This allows an interlocking arrangement to be created. The division of the sheet members into groups and the interlocking arrangement is described in more detail below.

Figure 2:
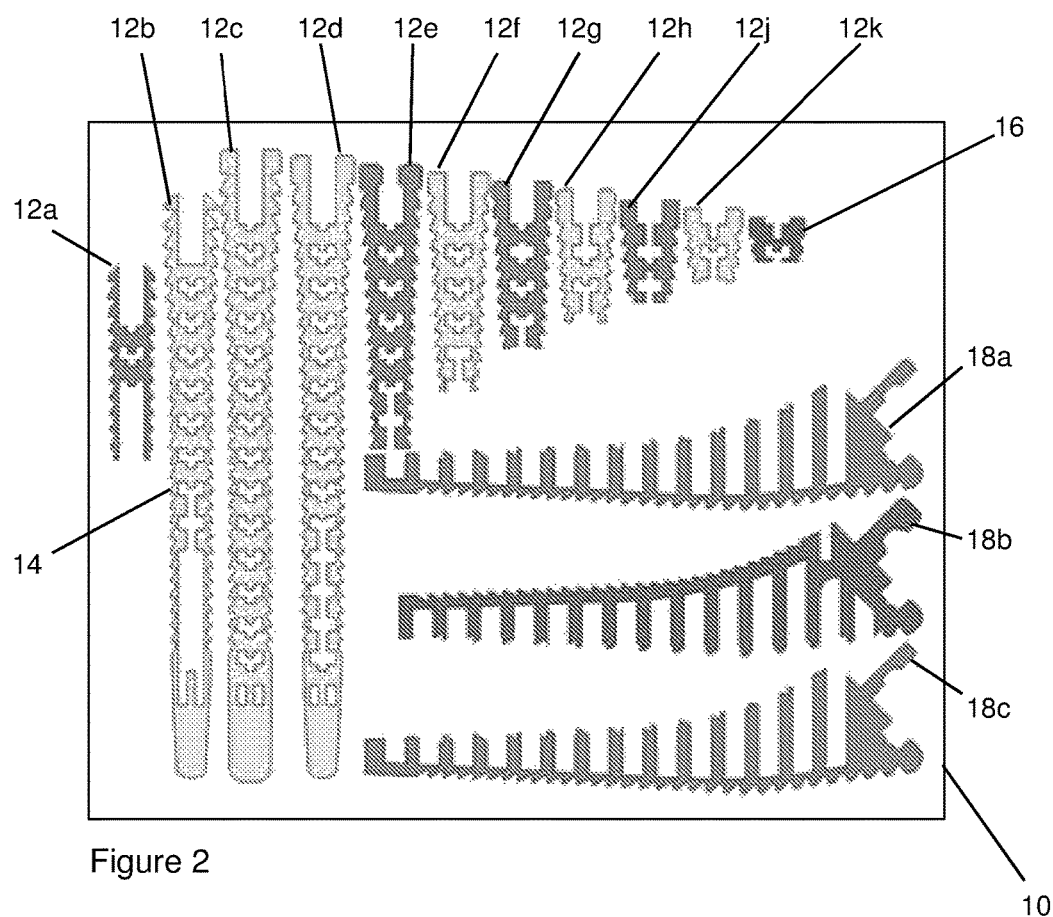
FIG. 2 shows the component pieces used to form the bone broach of FIG. 1 arranged on a single sheet of material.

FIG. 2 shows a sheet of material 10 from which the constituent components of a bone broach as depicted in FIG. 1 can be prepared. The constituent components comprise a first group of sheet members 12a Y 12k which form a first group. In the assembled bone broach 2, the first group define parallel planes and directly abut one of the other sheet members in the group. In addition, this first group all define at least one fully enclosed opening 14. A further member 16 is provided which is arranged in a plane parallel with the sheet members of the first group, but does not define a fully enclosed opening. The constituent components also include planar members 18a Y 18c which form a second group. In the assembled bone broach 2, the second group are arranged with their planes perpendicular to the planes of the first group in the assembled bone broach 2. Each of the sheet members of the second group comprise at least one protrusion 20 which extends within the plane defined by the member.

It is preferred that the individual sheet members are manufactured from stainless steel, and therefore the sheet 10 is a sheet of stainless steel. Preferably, the sheet has a thickness of around 2 mm, although other thicknesses may also be used. In alternate embodiments, other materials, including other metals or metal alloys may be used. As shown in FIG. 2, the size of the sheet of material 10 corresponds to an A4 sheet of paper (297 mm long by 210 mm wide). Thus, FIG. 2 depicts how the components sufficient to form a complete bone broach can be provided in an area less than half an A4 sheet of stainless steel.

It is preferred that the components are cut from the sheet of stainless steel 10 using chemical etching techniques. This is because the tooling costs for chemical etching are low and alternative tooling—for creation of broaches with different profiles and sizes—can be produced relatively simply. Etching also allows more complex shapes to provided with depth which varies at different locations on the plane of the sheet. This may allow more complex profiles to be manufactured to improve the cutting profile or interlocking of the sheet members. It also allows identification marking to be made on the sheet members, to assist in assembly or enable easy identification of the bone broach in use.

In alternative embodiments, the components may also be cut from the sheet of material 10 using any other suitable method. This includes stamping, laser cutting and waterjet cutting. Of these, stamping is less preferred due to the cost of tooling for each alternative broach configuration.

Figure 3:
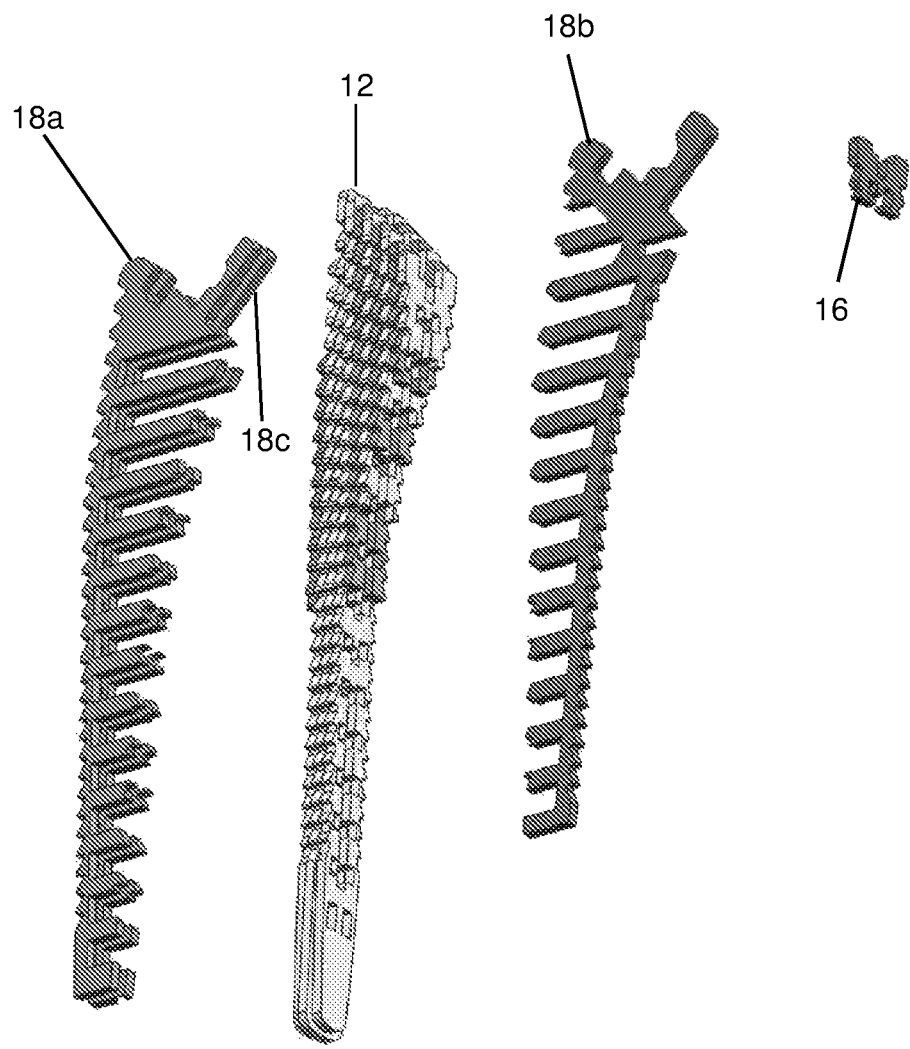
FIGS. 3 to 6 show stages in the assembly of a bone broach as shown in FIG. 1.

The construction of the bone broach 2 of FIG. 1 from the individual components 12a Y 12k, 16 and 18a Y 18c will now be described with reference to FIGS. 3-6. FIG. 3 depicts a first step in the construction of the bone broach. All of the sheet members 12 of the first group have been arranged abutting each other so that openings 14 are aligned with openings 14 in an adjacent sheet member 12. The sheet members 18a-18c of the second group are provided with their planes perpendicular to the planes defined by the sheet members 12 of the first group. They are arranged so that protrusions 20 can engage the aligned openings 14 in the first set of sheet members 12a-12k.

Figure 4:
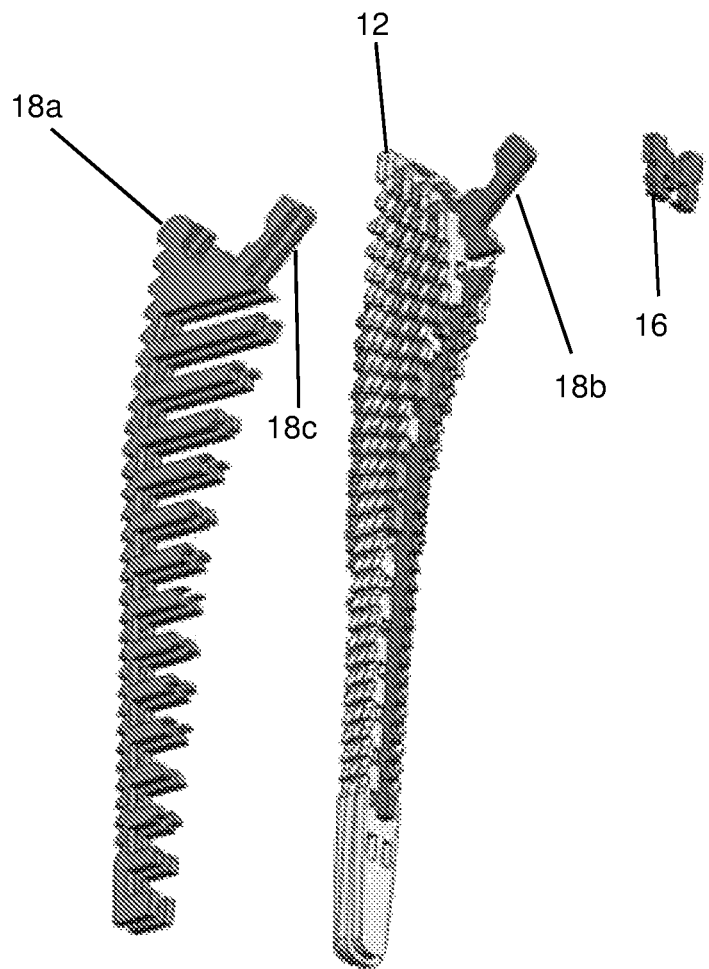

FIG. 4 depicts the next stage of assembly where sheet member 18c of the second group has been inserted so that its protrusions 20 engage aligned openings 14 in the first group. The protrusions 20 extend through the aligned openings so that their far end projects the other side and defines a cutting profile. At the opposite side of the cutting profile defined by protrusion 20, the edge of the component 18c itself defines a set of cutting teeth in a plane perpendicular to the cutting profiles defined by the edges of the group of sheet members 12. At this point in construction, the sheet member 18c of the second group interlocks with the sheet members 12 of the first group, preventing the sheet members 12 of the first group from moving within the plane they define because the protrusions 20 closely matches the dimensions of the openings 14 defined in the first group of sheet members.

Figure 5:
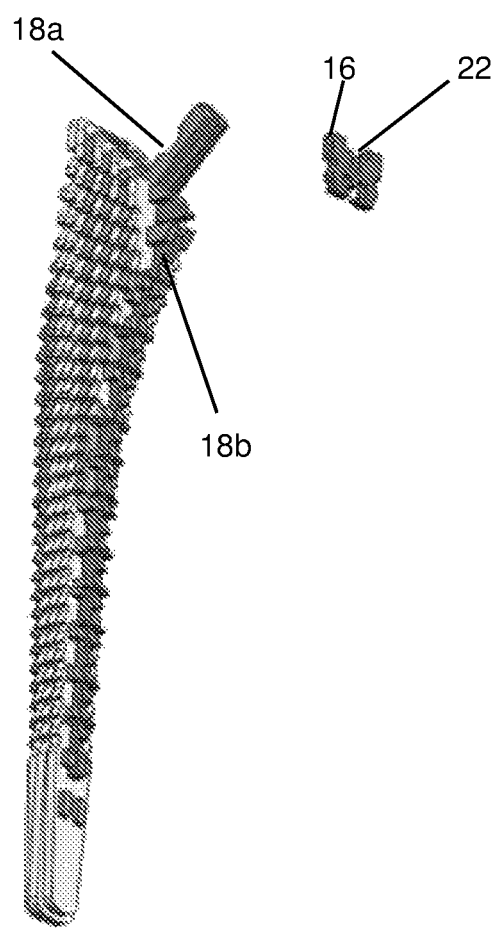
Figure 6:
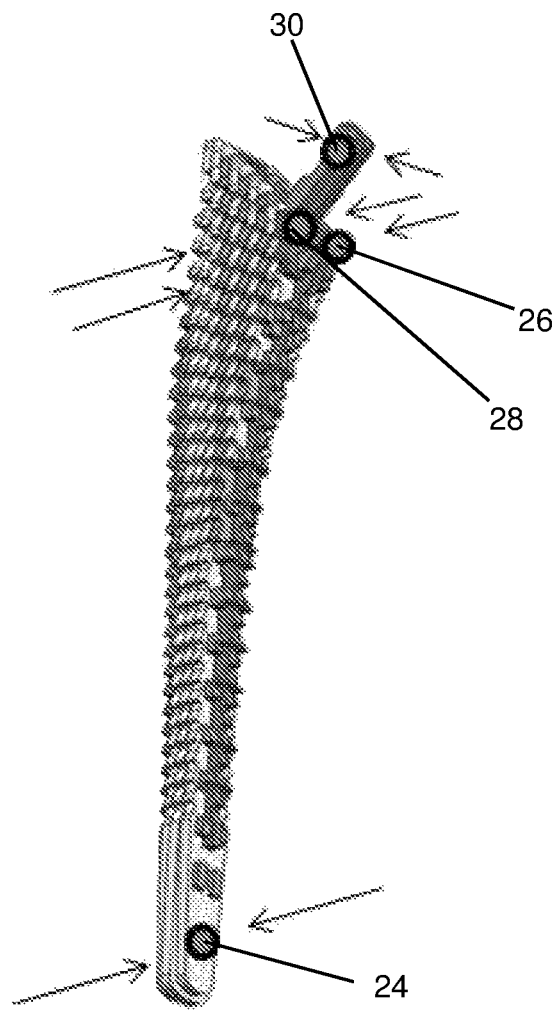

Next, as depicted in FIG. 5, the remaining sheet members 18a, 18b of the second group are inserted into aligned openings in the first group 12, from the opposite side than the sheet member 18c. This provides a further interlock with the sheet members 12. Together, the sheet members 18a, 18b, 18c of the second group define cutting profiles on the medial and lateral sides when the bone broach is for use in broaching a femur.

In the final step of assembly, sheet member 16 is placed in abutting contact with the elements 12 of the first group. Openings 22 in sheet member 15, which are not fully enclosed, engage protrusions in the components 18a-18c of the second group. This creates an interlocking set of plates.

Next, the plates are bonded together by spot welding at various points. In this embodiment, four spotwelds are formed at locations 24, 26, 28 and 30. As depicted by the arrows in FIG. 6, spotwelding is carried out by the application of electrodes at either side where the weld is required and passing an electric current between the electrodes. The electric current causes localised heating of the metal as it passes through it. The heating is sufficient to melt the metal in that location and weld the plates together.

Spotwelding is particularly advantageous in this application because it avoids the use of further bonding chemicals which might impact on the biocompatibility of the broach. However, in other embodiments, the individual sheet members may be bonded in other ways, for example using a glue or other form of adhesive between each plate and assembly. Other methods of bonding that may be used include mechanical fixations, such as screws, rivets, press fits or swaging. The elasticity of the base metal may be used to define clips within the sheet members themselves which engage adjacent sheet members to join them together.

The present invention therefore provides a bone broach which is cost effective and simple to manufacture, with minimum material and manufacturing costs. Depending on the desired form of the broach, the templates for the components cut from the sheet of material can be varied. The resulting broach comprises interlocked plates which because they are all substantially parallel to the longitudinal axis of the bone broach are not at risk of disconnection from each other during use.

A bone broach as discussed above may be produced in a variety of sizes. For example, depending on the ultimate size of the cavity required in the bone, a plurality of bone broaches of successively increasing sizes may be provided. In use, these are used in turn to progressively enlarge a cavity.

Figure 7:
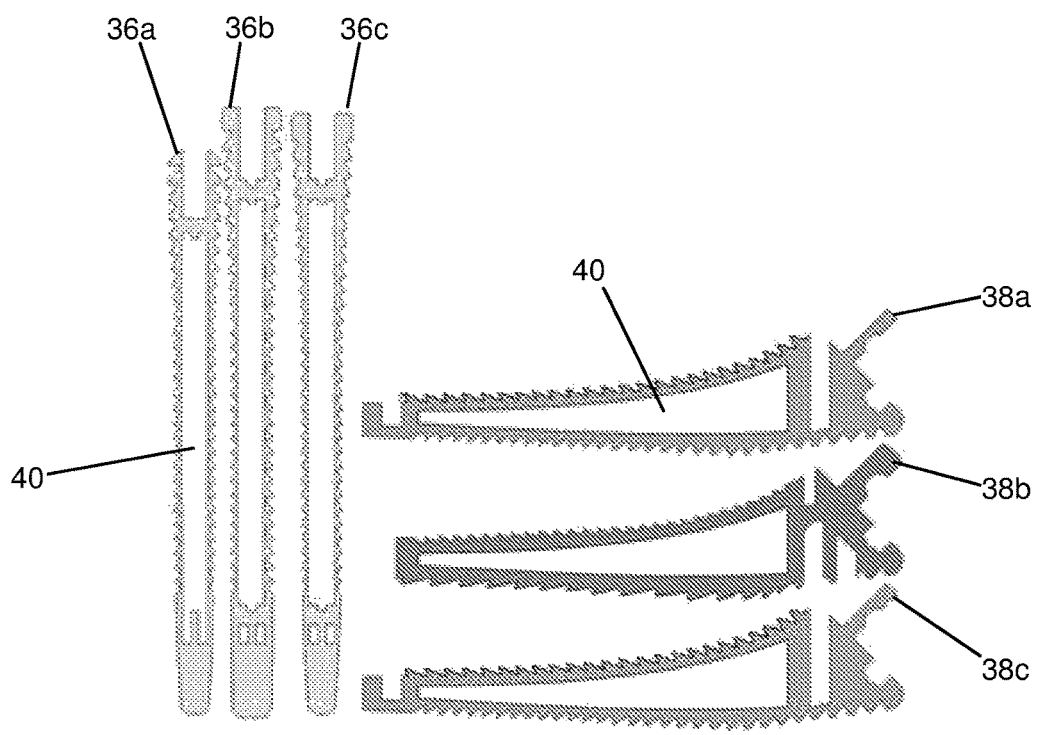
FIG. 7 shows a modification of the design of some of the component pieces shown in FIG. 1 to produce a partially hollow bone broach.

FIG. 7 depicts example sheet members 36, 38 from a further embodiment which is based on the construction depicted in FIG. 1. Here, at least some of the sheet members 36, 38 are modified to delimit a larger enclosed opening 40. Only the modified sheet members are depicted in FIG. 7 for clarity, the remainder of the sheet members are as depicted in FIG. 1.

The larger enclosed opening 40 provides more space than is needed to receive protrusions from other sheet members and form the structure of the bone broach. As a result the final construction includes hollow portions without defining gaps in the external profile. This can reduce the material cost and weight of the finished bone broach.

As depicted in FIG. 7, some of the sheet members in both the first group and the second group are provided with the larger enclosed opening 40. In alternate embodiment, only sheet members in one group may be provided with the larger enclosed opening.

In another embodiment, some of a system of bone broaches of different sizes may share the design of some of the sheet members with others of the system. For example larger bone broaches may use the same sheet members as a smaller broach together with additional sheet members which define the larger size. This is depicted in diagrammatic form by FIGS. 8 and 9.

Figure 8:
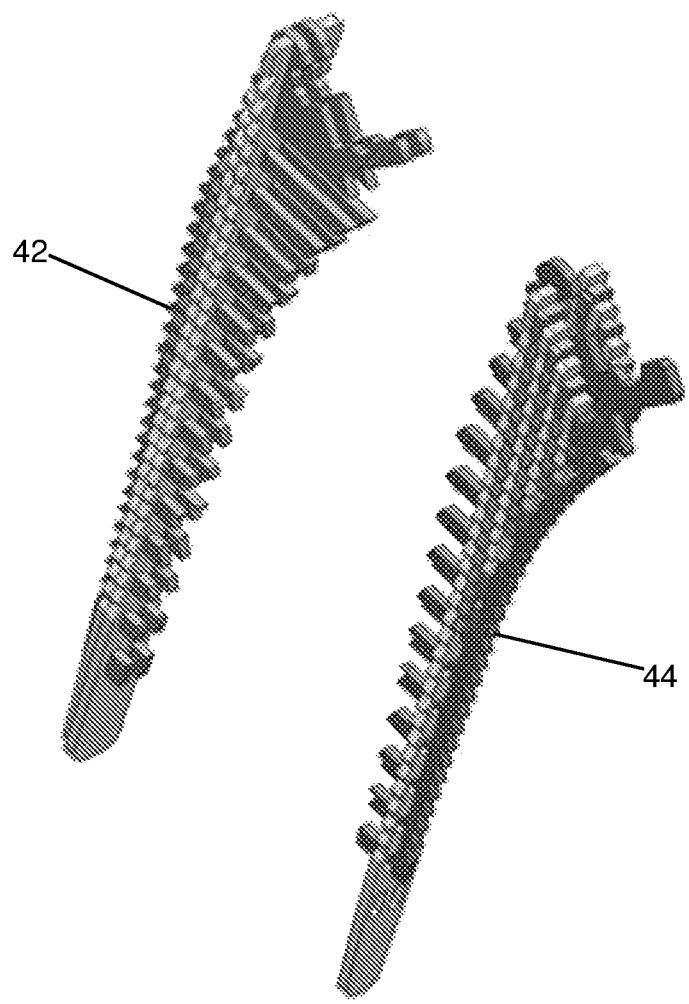
FIG. 8 is a partially exploded view of the bone broach of FIG. 1.
Figure 9:
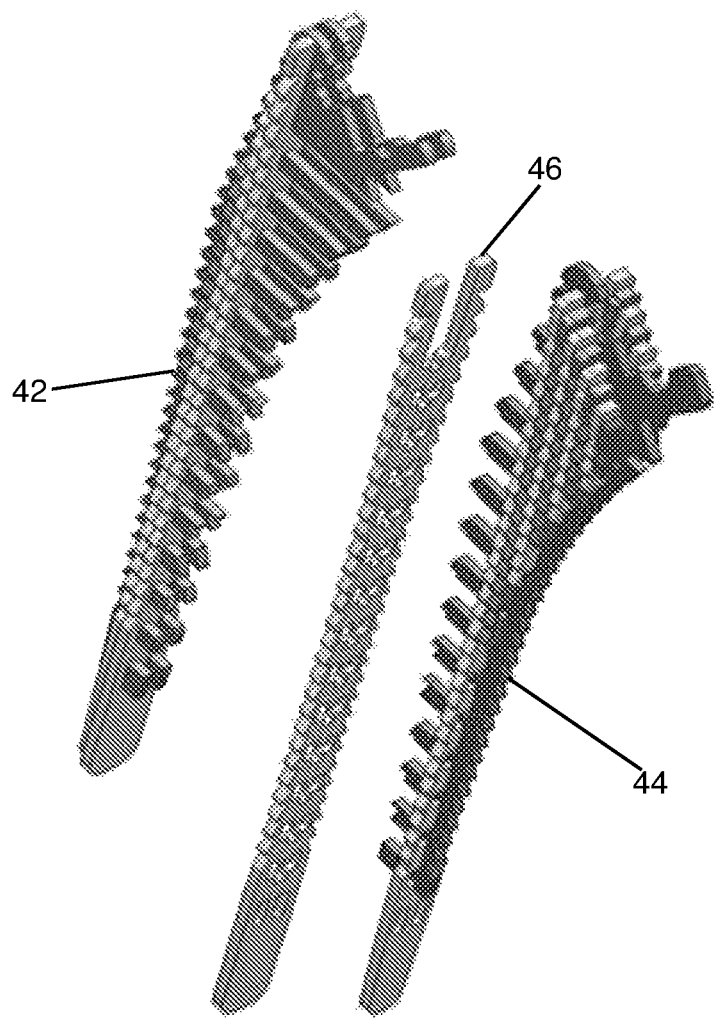
FIG. 9 is a partially exploded view of a bone broach of a larger size based on the design of the bone broach of FIG. 1.

FIG. 8 depicts a partially exploded view of the bone broach of FIG. 1. As depicted the bone broach comprises a first portion 42 and a second portion 44. FIG. 9 depicts how a bone broach of a larger size may be formed by reusing the design of the first portion 42 and second portion 44 and inserting a single additional sheet member 46. This allows the design of bone broaches of different sizes to be simplified.

As depicted in FIG. 9, all the sheet members of a smaller sized bone broach are reused to form a larger sized bone broach. However, this is not essential and alternative embodiments may reuse fewer than all the sheet members and still obtain the benefit of simplified construction and design.

It is contemplated that the present invention could be used in a system consisting entirely of bone broaches produced according to the invention. However, a higher quality finish may be provided if the final shape of the cavity is created using a bone broach which is not made of sheet members, for example a conventional machined bone broach or a bone broach made by any other process, such as direct metal sintering, casting, MIM, or plastic injection moulding. In that case, the present invention forms part of a system comprising a plurality of bone broaches formed as described above, and a single bone broach formed by machining. In that case, the higher cost of the machined final stage broach means it is preferable that it will be a reusable instrument. In contrast, the bone broaches formed according to the method of the invention above are intended for single use. The instrumentation cost and requirement for decontamination/sterilisation after surgery is therefore reduced because only one more expensive bone broach is reused and required to be decontaminated/sterilised after use.

The invention claimed is:

1. A method of manufacturing a bone broach, the method comprising:
    (a) preparing a plurality of substantially planar members of which at least some define at least one cutting profile at their perimeters,
    (b) arranging the plurality of substantially planar members into:
        a first group of substantially planar members defining planes which are substantially parallel to each other, and
        at least one additional substantially planar member, which is a separate component from the first group of substantially planar members, and
    (c) joining the plurality of substantially planar members together, that the at least one additional substantially planar member defines a plane which, when the at least one substantially planar member is assembled with the first group of substantially planar members, is angled relative to the planes defined by the first group of substantially planar members;
    wherein, when the first group of substantially planar members is assembled with the additional substantially planar member, the assembled bone broach defines a three-dimensional structure with an external profile corresponding to the shape to be created in a bone by the broach.

2. The method of claim 1, in which the preparing step comprises cutting or etching from a sheet of material.

3. The method of claim 2, in which the preparing step comprises cutting or etching the plurality of substantially planar members from the same sheet of material.

4. The method of claim 1, in which the additional substantially planar member is one of a second group of planar members, the second group of planar members which define planes which are substantially parallel to one another in the assembled broach, the planes defined by the second group of planar members being angled relative to the planes defined by the first group.

5. The method of claim 4, in which the second group of substantially planar members define planes which are arranged in the arranging step so that they substantially perpendicular to the planes defined by the first group of substantially planar members.

6. The method of claim 4, in which the arranging step includes forming interlocking stacks from the first group and the second group.

7. The method of claim 1, in which the preparing step includes:
    defining at least one opening in each substantially planar member of the first group, and
    defining at least one protrusion in the additional substantially planar member or each substantially planar member of the second group,
and in which the arranging step includes engaging an opening in at least one substantially planar member of the first group with a protrusion of additional substantially planar member or at least one substantially planar member of the second group.

8. The method of claim 7, in which the arranging step includes:
    aligning at least one opening in each substantially planar member of the first group with an opening in a directly adjacent substantially planar member of the first group, thereby creating an aligned opening, and
    engaging the aligned opening with a protrusion of the additional substantially planar member or at least one substantially planar member of the second group.

9. The method of claim 8, in which the arranging step includes aligning directly adjacent substantially planar members of the first group such that the aligned opening extends through the first group in a direction perpendicular to the planes defined by the first group.

10. The method of claim 9, in which the arranging step includes engaging a protrusion of at least one substantially planar member of the second group with the aligned opening, such that the protrusion extends out of the opening and defines at least one cutting profile.

11. The method of claim 1, in which the plurality of substantially planar members comprise a metal or metal alloy and the joining comprises spot welding.

12. A method of manufacturing a system of at least two bone broaches of different sizes, the method comprising manufacturing each bone broach according to the method of claim 1, in which the shape of at least one of the substantially planar members is the same in at least two of the bone broaches.

* * * * *